US006369218B1

(12) United States Patent
Cainelli et al.

(10) Patent No.: US 6,369,218 B1
(45) Date of Patent: Apr. 9, 2002

(54) ISOMERISATION OF 6β-FLUOROSTEROIDS INTO THE CORRESPONDING 6α-FLUORO DERIVATIVES

(75) Inventors: Gianfranco Cainelli; Achille Umani-Ronchi; Michele Contento, all of Bologna; Sergio Sandri, Forli' ; Marco Da Col, Bologna, all of (IT)

(73) Assignee: Farmabios S.r.L, Gropello Cairoli (IT)

( * ) Notice: Subject to any disclaimer, the term of this patent is extended or adjusted under 35 U.S.C. 154(b) by 0 days.

(21) Appl. No.: 09/858,407

(22) Filed: May 16, 2001

(30) Foreign Application Priority Data

Nov. 15, 2000 (IT) .......................................... MI00A2454

(51) Int. Cl.⁷ .............................. C07J 5/00; C07J 71/00
(52) U.S. Cl. .......................... 540/48; 540/63; 552/565; 552/586; 552/593

(58) Field of Search ................................. 552/565, 586, 552/593; 540/48, 63

(56) References Cited

U.S. PATENT DOCUMENTS

| 3,681,410 A | * | 8/1972 | Crabbe et al. ........... 260/397.3 |
| 4,036,831 A | * | 7/1977 | Loken et al. ........... 260/239.55 |
| 4,340,538 A | * | 7/1982 | Shephard ............... 260/239.55 |

* cited by examiner

*Primary Examiner*—Barbara P. Badio
(74) *Attorney, Agent, or Firm*—Hedman & Costigan, P.C.

(57) ABSTRACT

Described herein is the isomerisation process of 6β-fluorosteroids into the corresponding pharmacologically active 6α-fluoro derivatives, comprising the reaction of 6β-fluorosteroids, or 6α/6β isomeric mixtures, with an organic base containing a diazoimino group in a suitable organic solvent.

9 Claims, No Drawings

ISOMERISATION OF 6β-FLUOROSTEROIDS INTO THE CORRESPONDING 6α-FLUORO DERIVATIVES

FIELD OF THE INVENTION

The present invention refers to a process for the conversion of 6β-fluoro derivatives into the corresponding 6α-fluoro derivatives of pregnane compounds of formula (I) reported hereinafter, useful as intermediates for the preparation of anti-inflammatory pharmaceutical formulations.

PRIOR ART

6α-fluoro substituted isomers of pregnane derivatives exert a pharmacological action, which makes them useful in the preparation of anti-inflammatory pharmaceutical formulations. Conversely, the corresponding 6β-fluoro derivatives do not exert any pharmacological action.

A number of procedures for the preparation of 6-fluoro pregnane derivatives have been developed so far. However, all of them yield mixtures of the two isomers with relatively high 6β/6α ratios. It follows that, to obtain the pharmacologically active isomer only, isomer 6β must be converted into isomer 6α.

By way of example, U.S. Pat. No. 2,961,441 discloses a process for the preparation of 6-fluoro substituted pregnane derivatives, which yields isomer 6β. This isomer is then converted into the corresponding isomer 6α by treatment with an acid or a base, such as HCl or KOH, in an appropriate organic solvent, such as acetic acid, chloroform, methanol or ethanol.

U.S. Pat. No. 3,980,778 describes the preparation of a 6α-fluoro substituted pregnane derivative by fluorination of a suitable substrate. Said reaction yields a 6β/6α isomeric mixture in which isomer 6β predominates. According to said patent, the conversion of isomer 6β into the corresponding isomer 6α may be carried out e.g. by treatment with HCl or with a dimethylformamide-HCl complex in an inert organic solvent, such as chloroform or chloroform-ethanol mixtures.

Still unresolved is the problem of converting 6β-fluorosteroids into the corresponding pharmacologically active 6α-fluoro derivatives by means of processes not requiring drastic reaction conditions, though maintaining short reaction times. Said drastic conditions would make the process inapplicable to substrates with unstable functional groups, e.g. epoxides, esters or acetals.

SUMMARY OF THE INVENTION

It has surprisingly been found that it is possible to obtain a mixture of isomers with a 6α/6β ratio above 95:5 also starting from pure isomer 6β or from mixtures in which isomer 6β predominates, simply by treating the starting mixture in an opportunely selected organic solvent with an organic base containing a diazoimino group.

It is, therefore, an object of the present invention to provide a process for the isomerisation of 6β-fluoro derivatives into the corresponding 6α-fluoro derivatives of pregnane compounds of formula (I), comprising the reaction of 6β-fluorosteroids, or of 6α/6β isomeric mixtures, with an organic base, to obtain a 6α-enriched 6α/6β mixture with a 6α/6β ratio higher than 95:5

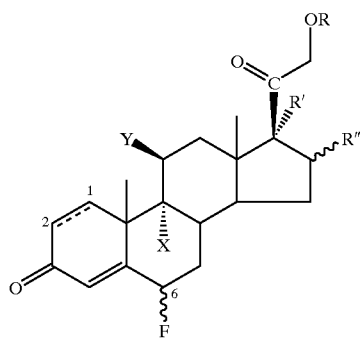

where R is H or an acyl group containing 1 to 5 carbon atoms in the alkyl chain; R' is OH or an acyloxy group containing 1 to 5 carbon atoms in the alkyl chain; R" is H or a methyl group; or R' e R", taken together, form a

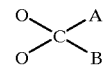

group, in which A and B, identical or different from each other, are H or an alkyl group containing 1 to 4 carbon atoms; X is H, Y is OH or a carbonyl group; or X and Y, taken together, are an epoxy group, and where a double bond may be present between positions 1 and 2. said isomerisation process being characterised by the fact that the organic base contains a diazoimino group and the reaction is carried out in an aprotic polar organic solvent.

DETAILED DESCRIPTION OF THE INVENTION

The present process allows the obtainment of 6-fluoro substituted pregnane derivatives of formula (I) in the form of 6α-enriched isomeric mixtures with a 6α/6β ratio higher than 95:5, through a simple basic isomerisation that yields the final product starting from pure isomer 6β or from mixtures with any 6α/6β ratio. In the process according to the present invention preferred are the pregnane derivatives of formula (I) above reported wherein X and Y, taken together, are an epoxy group.

The 6α/6β ratio of the final product was determined by NMR analysis and was found to be higher than 95:5.

Compared with the processes of the prior art, the reaction of the present invention is surprisingly advantageous because, under mild reaction conditions and within much shorter reaction times, it gives high-purity 6α-fluorosteroids of formula (I) in high yields.

According to the present invention, the starting compound is caused to react with an organic base containing a diazoimino group, selected e.g. from the group consisting of 1,8-diazabicyclo[5.4.0]undec-7-ene(1,5-5)(DBU), 1,5-diazabicyclo[4.3.0]non-5-ene (DBN), and 1,1,3,3-tetramethylguanidine.

According to a preferred embodiment of the present process the organic base used is 1,8-diazabicyclo[5.4.0]undec-7-ene(1,5-5)(DBU).

Preferably the molar ratio between the organic base and the pregnane derivative of formula (I) ranges between 1:1 and 2:1, and more preferably is 1.3:1.

The solvent used in the present isomerisation process is any aprotic polar organic solvent; furthermore, to obtain the advantages described above, also solvents in the non-anhydrous form may be used.

According to a preferred embodiment of the present invention, the reaction solvent used is selected from the group consisting of dimethylformamide, tetrahydrofuran, acetone and acetonitrile.

The process of the invention may be carried out at room temperature, generally at a temperature ranging from 0 to 50° C.

According to the present invention, the reaction times range between 3 and 48 hrs. The following examples are conveyed by way of indication, not of limitation, of the present invention.

EXAMPLE 1

Preparation of 6α-fluoro-9β, 11β-epoxy-16α-methyl-3,20-diketo-17α,21-dihydroxy-1,4-pregnadiene 6-fluoro-9β,11β-epoxy-16α-methyl-3,20-diketo-17α,21-dihydroxy-1,4-pregnadiene (0.26 mmol) in the form of an isomeric mixture with a 6α/6β ratio of 85:15 in dimethylformamide (1.5 ml) was added with DBU (0.33 mmol) at room temperature. The reaction mixture was kept under stirring for approx. 12 hrs.

After approx. 12 hrs, when the isomerisation was complete, the solution was added dropwise to cold water, slightly acidified by addition of hydrochloric acid and the precipitate was filtered under vacuum. The solid crude obtained was analysed by $^1$H-NMR (CDCl$_3$, 200 MHz): δ0.95 (d, 3H, J=7 Hz), 1.05 (s, 3H), 1.42 (s, 3H), 3.20 (m, 1H), 3.36 (b.s., 1H), 4.33 (system AB, 2H, J=18 Hz), 5.45 (dddd, 1H, J=50,10, 6, 2 Hz), 6.20 (d, 1H, J=10 Hz). 6,39 (s,1H), 6.55 (d,1H, J=10 Hz).

The reaction gave isomer 6α in 80% yield.

EXAMPLE 2

Preparation of 6α-fluoro-9β,11β-egoxy-16α-methyl-3,20-diketo-1,4-pregnadiene 17α,21-diacetate 6-fluoro-9β,11β-epoxy-16α-methyl-3,20-diketo-1,4-pregnadiene-17α,21-diacetate (1 mmol) in the form of an isomeric mixture with a 6α/6β ratio of 38:62 in acetone (5 ml) was added with DBN (1.3 mmol) at room temperature. The reaction mixture was kept under stirring.

After approx. 48 hrs, when the isomerisation was complete, the solution was concentrated by rotavapor and the residue was dissolved in dimethylformamide. The resulting mixture was added dropwise to slightly acid cold water and the precipitate was filtered under vacuum.

The solid crude obtained was analysed by $^1$H-NMR (CDCl$_3$ 200 MHz) δ0,96 (d, 3H, J=7 Hz), 0.99 (s, 3H), 1.42 (s, 3H), 2.13 (s, 3H), 2.19 (s, 3H), 2.67 (m, 1H), 3.18 (m, 1H), 3.32 (b.s., 1H), 4.76 (m, 2H), 5.46 (dddd, 1H J=50, 10, 6, 2 Hz), 6.28 (dd, 1H, J=2,10 Hz), 6.47 (m, 1H), 6.54 (d, 1H, J=10 Hz). The reaction gave isomer 6α in 80% yield.

EXAMPLE 3

Preparation of 6α-fluoro-9β,11β-epoxy-16α-methyl-3,20-diketo-1,4-pregnadiene 17α,21-diacetate 6-fluoro-9β,11β-epoxy-16α-methyl-3,20-diketo-1,4-pregnadiene-17α,21-diacetate (1 mmol) in the form of an isomeric mixture with a 6α/6β ratio of 38:62 in dimethylformamide (5 ml) was added with DBN (1.3 mmol) at room temperature. The reaction mixture was kept under stirring.

After approx. 48 hrs, when the isomerisation was complete, the solution was added dropwise to slightly acid cold water and the precipitate was filtered under vacuum. The solid crude obtained was analysed by $^1$H-NMR.

The reaction gave isomer 6α in 88% yield.

EXAMPLE 4

Preparation of 6α-fluoro-9β,11β-epoxy-16α-methyl-3,20-diketo-1,4-pregnadiene 17α,21-diacetate The method of Example 3 was followed except that 1,1,3,3-tetramethylguanidine replaced DBN. In this case, the isomerisation was completed in approx. 12 hrs.

The reaction gave isomer 6α in 88% yield.

EXAMPLE 5

Preparation of 6α-fluoro-9β,11β-epoxy-16α-methyl-3,20-diketo-1,4-pregnadiene 17α,21-diacetate The method of Example 2 was followed except that DBU replaced DBN. In this case, the isomerisation was completed in approx. 12 hrs.

The reaction gave isomer 6α in 80% yield.

EXAMPLE 6

Preparation of 6α-fluoro-9β,11β-epoxy-3,20-diketo-1,4-pregnadiene 17α,21-diacetate 6-fluoro-9β,11β-epoxy-3,20-diketo-1,4-pregnadiene-17α,21-diacetate (0.44 mmol) in the form of an isomeric mixture with a 6α/6β ratio of 85:15 in acetonitrile (3 ml) was added with DBU (0.57 mmol) at room temperature. The reaction mixture was kept under stirring.

After approx. 48 hrs, when the isomerisation was complete, the solution was added dropwise to slightly acid cold water and the precipitate was filtered under vacuum. The solid crude was analysed by $^1$H-NMR (CDCl$_3$, 200 MHz) δ0,91 (s, 3H), 1.41 (s, 3H), 2.07 (s, 3H), 2.15 (s, 3H), 2.36 (m, 1H), 2.70 (m, 1H), 3.32 (b.s., 1H), 4.75 (system AB, 2H, J=18 Hz), 5.42 (ddd, 1H, J=50, 10, 6 Hz), 6.25 (d, 1H, J=10 Hz), 6.45 (s, 1H), 6.55 (d, 1H, J=10 Hz).

The reaction gave isomer 6α in 65% yield.

EXAMPLE 7

Preparation of 6α-fluoro-9β,11β-epoxy-3,20-diketo-1,4-pregnadiene 17α,21-diacetate The method of Example 6 was followed except that acetone replaced acetonitrile and DBN replaced DBU. The same results were obtained.

EXAMPLE 8

Preparation of 6α-fluoro-9β11β-epoxy-3,20-diketo-16,17-isopropylidenedioxy-1,4-pregnadiene 21-acetate 6α-fluoro-9β,11β-epoxy-3,20-diketo-16,17-isopropylidenedioxy-1,4-pregnadiene 21-diacetate (2.11 mmol) in the form of an isomeric mixture with a 60/6β ratio of 25:75 in dimethylformamide (10 ml) was added with DBN (2.74 mmol) at room temperature. The reaction mixture was kept under stirring.

After approx. 12 hrs, when the isomerisation was complete, the solution was added dropwise to slightly acid cold water and the precipitate was filtered under vacuum. The solid crude obtained was analysed by $^1$H-NMR (CDCl$_3$, 200 MHz) δ0.84 (s, 3H), 1.22 (s, 3H), 1.42 (s, 3H), 1.46 (s, 3H), 2.18 (s, 3H), 2.40 (m, 1H), 2.69 (m, 1H), 3.34 (b.s., 1H), 4.89 (system AB, 2H, J=18 Hz), 5.00 (m, 1H) 5.45 (dddd, 1H, J=50, 10, 6, 2 Hz), 6.28 (dd, 1H, J=2, 10 Hz), 6.47 (m, 1H), 6.55 (dd, 1H, J=1,8, 10Hz).

The reaction gave isomer 6α in 75% yield.

EXAMPLE 9

Preparation of 6α-fluoro-9β,11β-epoxy-3,20-diketo-16,17-isopropylidenedioxy-1,4-pregnadiene 21-acetate The method of Example 8 was followed except that 1,1,3,3-tetramethylguanidine replaced DBN. The same results were obtained.

EXAMPLE 10

Preparation of 6α-fluoro-9β,11β-epoxy-3,20-diketo-16,17-isopropylidenedioxy-1,4-pregnadiene 21-acetate 6-fluoro-9β,11β-epoxy-3,20-diketo-16,17-isopropylidenedioxy-1,4-pregnadiene 21-acetate (2.11 mmol) in the form of isomeric mixture with a 6α/6β ratio of 25:75 in tetrahydrofuran (10 ml) was added with DBU (2.74 mmol) at room temperature. The reaction mixture was kept under stirring.

After approx. 24 hrs, when the isomerisation was complete, the solution was concentrated by rotavapor and the oil residue was dissolved in dimethylformamide. The resulting mixture was added dropwise to slightly acid cold water and the precipitate was filtered under vacuum. The solid crude obtained was analysed by $^1$H-NMR.

The reaction gave isomer 6α in 70% yield.

EXAMPLE 11

Preparation of 6α-fluoro-9β,11β-epoxy-3,20-diketo-16,17-isopropylidenedioxy-1,4-pregnadiene 21-acetate The method of Example 10 was followed except that the solvent used was acetonitrile instead of tetrahydrofuran. The same results were obtained.

EXAMPLE 12

Preparation of 6α-fluoro-9β,11β-epoxy-3,20-diketo-16,17-isopropylidenedioxy-1,4-pregnadiene 21-acetate The method of Example 10 was followed except that the solvent used was acetone instead of tetrahydrofuran. The same results were obtained.

What is claimed is:

1. An isomerisation process of 6β-fluoro derivatives into the corresponding 6α-fluoro derivatives of pregnane compounds of formula (I), comprising the reaction of 6β-fluorosteroids, or 6α/6β isomeric mixtures, with an organic base, to obtain a 6α-enriched 6α/6β mixture with a 6α/6β ratio higher than 95:5

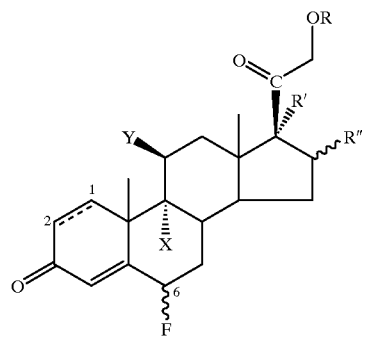

(I)

where R is H or an acyl group containing 1 to 5 carbon atoms in the alkyl chain; R' is OH or an acyloxy group containing 1 to 5 carbon atoms in the alkyl chain; R' is H or a methyl group; or R' and R", taken together, form a

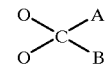

group, in which A and B, identical or different from each other, are H or an alkyl group containing 1 to 4 carbon atoms; X is H, Y is OH or a carbonyl group; X and Y, taken together, are an epoxy group, and where a double bond may be present between positions 1 and 2;

is said isomerisation process being characterised by the fact that the said organic base contains a diazoimino group and the reaction is carried out in an aprotic polar organic solvent.

2. The process as claimed in claim 1, wherein in the said pregnane compounds of formula (I) X and Y, taken together, are an epoxy group.

3. The process as claimed in claim 1, wherein said organic base is selected from the group consisting of 1,8-diazabicyclo[5.4.0. ]undec-7-ene(1,5-5)(DBU), 1,5-diazabicyclo[4.3.0. ]non-5-ene (DBN), and 1,1,3,3-tetramethylguanidine.

4. The process as claimed in claim 2, wherein said organic base is 1,8-diazabicyclo[5.4.0]undec-7-ene(1,5-5)(DBU).

5. The process as claimed in claim 1, wherein said aprotic polar organic solvent is selected from the group consisting of dimethylformamide, tetrahydrofuran, acetone and acetonitrile.

6. The process as claimed in claim 1, wherein the reaction temperature ranges from 0 to 50° C.

7. The process as claimed in claim 1, wherein the reaction time ranges from 3 to 48 hrs.

8. The process as claimed in claim 1, wherein the molar ratio between the said organic base and the said pregnane compound of formula (I) ranges between 1:1 and 2:1.

9. The process as claimed in claim 8, wherein the said molar ratio is 1.3:1.

* * * * *